(12) United States Patent
Hannon (10) Patent No.: US 7,833,169 B2
(45) Date of Patent: Nov. 16, 2010

(54) DEVICE AND METHOD FOR THE COLLECTION OF A URINE SAMPLE

(75) Inventor: David Hannon, Co. Mayo (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 12/015,912

(22) Filed: Jan. 17, 2008

(65) Prior Publication Data

US 2008/0188770 A1  Aug. 7, 2008

Related U.S. Application Data

(60) Provisional application No. 60/898,082, filed on Jan. 29, 2007.

(51) Int. Cl.
*A61B 5/00* (2006.01)
*B65D 81/00* (2006.01)
*A61M 1/00* (2006.01)

(52) U.S. Cl. ............... 600/573; 600/574; 600/575; 604/327; 604/328; 604/329; 604/330; 604/331

(58) Field of Classification Search ............ 600/572, 600/573–575; 604/327–331
See application file for complete search history.

(56) References Cited

U.S. PATENT DOCUMENTS

| | | | | |
|---|---|---|---|---|
| 2,749,913 | A | * | 6/1956 | Wallace ............ 604/129 |
| 3,369,546 | A | * | 2/1968 | Hickok ............ 604/349 |
| 3,428,046 | A | | 2/1969 | Remer et al. |
| 3,513,849 | A | | 5/1970 | Vaillancourt et al. |
| 3,575,158 | A | | 4/1971 | Summers |
| 3,817,239 | A | | 6/1974 | Kuntz |
| 4,106,675 | A | | 8/1978 | Taylor |
| 4,109,837 | A | | 8/1978 | Taylor |

(Continued)

FOREIGN PATENT DOCUMENTS

CA    2351489 A1    6/2000

(Continued)

OTHER PUBLICATIONS

International Search Report issued in PCT/US2008/051307 (4 pages).

(Continued)

*Primary Examiner*—Max Hindenburg
*Assistant Examiner*—Sean P Dougherty
(74) *Attorney, Agent, or Firm*—Marshall, Gerstein & Borun LLP (57) ABSTRACT

A device and method for collection of a urine sample is disclosed which comprises a channel, an opening in the channel, and a collector associated with the opening. The channel is formed so that urine can flow through it from a first end to a second end thereof. The opening is provided in the channel at a point between the first and the second ends thereof. The collector is associated with the opening in the channel to be able to receive urine therein. In one embodiment, a member can cover the opening to permit urine to pass through it after contact with urine. Specifically, the member may dissolve or otherwise permit urine to pass through the opening after a period of time to test a urine sample which is not from the initial flow of urine to avoid bacteria contamination.

47 Claims, 7 Drawing Sheets

U.S. PATENT DOCUMENTS

| | | | |
|---|---|---|---|
| 4,116,227 A | 9/1978 | Eisenberg et al. | |
| 4,168,699 A | 9/1979 | Hauser | |
| 4,203,169 A * | 5/1980 | Dale | 73/863.52 |
| 4,204,527 A | 5/1980 | Wu et al. | |
| 4,205,690 A | 6/1980 | Layton | |
| 4,246,909 A | 1/1981 | Wu et al. | |
| 4,423,741 A * | 1/1984 | Levy | 600/581 |
| 4,492,258 A * | 1/1985 | Lichtenstein et al. | 141/1 |
| 4,503,864 A | 3/1985 | Powers | |
| 4,557,274 A * | 12/1985 | Cawood | 600/573 |
| 4,717,658 A | 1/1988 | Michaels | |
| 4,771,484 A | 9/1988 | Mozell | |
| 4,852,560 A | 8/1989 | Hermann, Jr. et al. | |
| 4,911,698 A | 3/1990 | Wapner | |
| 5,147,341 A * | 9/1992 | Starke et al. | 604/349 |
| 5,251,639 A | 10/1993 | Rentsch | |
| 5,531,717 A | 7/1996 | Roberto et al. | |
| 5,616,138 A | 4/1997 | Propp | |
| 5,711,841 A | 1/1998 | Jaker | |
| 5,725,515 A | 3/1998 | Propp | |
| 5,766,136 A * | 6/1998 | Cawood | 600/573 |
| 5,897,535 A | 4/1999 | Feliziani et al. | |
| 5,919,146 A | 7/1999 | Propp | |
| 6,150,178 A | 11/2000 | Cesarczyk et al. | |
| 6,355,004 B1 | 3/2002 | Pedersen et al. | |
| 6,537,262 B2 * | 3/2003 | Thompson | 604/347 |
| 6,558,350 B1 * | 5/2003 | Hart et al. | 604/104 |
| 6,821,788 B2 | 11/2004 | Cesarczyk | |
| 7,011,634 B2 * | 3/2006 | Paasch et al. | 600/573 |
| 7,160,256 B2 | 1/2007 | Perlhagen et al. | |
| 7,172,559 B2 * | 2/2007 | Yong et al. | 600/573 |
| 7,195,602 B2 * | 3/2007 | Yong et al. | 600/573 |
| 7,435,242 B2 * | 10/2008 | Levinson | 604/329 |
| 7,547,298 B2 * | 6/2009 | Lee et al. | 604/319 |
| 2002/0106809 A1 | 8/2002 | Cesarczyk | |
| 2002/0193760 A1 * | 12/2002 | Thompson | 604/318 |
| 2003/0124618 A1 | 7/2003 | Chen et al. | |
| 2003/0143755 A1 | 7/2003 | Davis et al. | |
| 2003/0195478 A1 | 10/2003 | Russo | |
| 2003/0207465 A1 | 11/2003 | Davis et al. | |
| 2003/0219908 A1 | 11/2003 | Davis et al. | |
| 2004/0092036 A1 | 5/2004 | Chen et al. | |
| 2004/0267158 A1 * | 12/2004 | Paasch et al. | 600/573 |
| 2004/0267159 A1 * | 12/2004 | Yong et al. | 600/575 |
| 2005/0004493 A1 * | 1/2005 | Yong et al. | 600/575 |
| 2005/0220668 A1 | 10/2005 | Coville | |
| 2005/0240164 A1 | 10/2005 | Perlhagen et al. | |
| 2006/0064033 A1 * | 3/2006 | Stewart et al. | 600/573 |
| 2006/0064034 A1 * | 3/2006 | Stewart et al. | 600/573 |
| 2006/0184064 A1 * | 8/2006 | Paasch et al. | 600/573 |
| 2008/0177201 A1 * | 7/2008 | Deadwyler et al. | 600/573 |

FOREIGN PATENT DOCUMENTS

| | | |
|---|---|---|
| EP | 0605427 B1 | 7/1994 |

OTHER PUBLICATIONS

Written Opinion issued in PCT/US2008/051307 (6 pages).

* cited by examiner

| | NEGATIVE | POSITIVE | | | | | |
|---|---|---|---|---|---|---|---|
| Nitrite | | | | | | | |
| Leucocytes | | | | | | | |
| | 5.0 | 6.0 | 6.5 | 7.0 | 7.5 | 8.0 | 8.5 |
| pH | ▨ | ▨ | | ▨ | ▨ | ▨ | ▨ |

DEVICE AND METHOD FOR THE COLLECTION OF A URINE SAMPLE

CROSS-REFERENCE TO RELATED APPLICATION

This application claims priority to U.S. Provisional Patent Application No. 60/898,082, filed Jan. 29, 2007.

FIELD OF THE DISCLOSURE

The present disclosure generally relates to a device and method for the collection of a biologic specimen or sample from the human body, and more particularly, to a device and method for the collection of a urine sample.

BACKGROUND OF THE DISCLOSURE

It is well-known to use the principle of midstream urine sample collection as the recommended procedure when testing for urinary tract conditions. The primary basis for using this procedure is because of recognition and understanding of health care professionals that the initial flow of urine from a patient almost always contains a significant level of bacteria. In particular, the initial flow of urine contains bacteria from the flow of urine through the urethral entrance as well as the urethra itself.

As a result, health care professionals try to avoid collecting the initial flow of urine to thereby exclude much of the bacteria from the sample to avoid interfering with the test that is conducted on the sample. Usually the current practice in collecting a midstream sample involves instructing the patient to clean the meatus with soap and water and then begin urination and, after a short time, to place a cup within the urine flow to collect a urine sample which can be tested for urinary tract infections. Once the sample is collected it is then tested by sending the sample to a laboratory for culture and sensitivity (requiring the user to refrigerate the sample until it can be taken to a lab for testing or obtaining the specimen at the healthcare professional's office/clinic). Current dip stick measurement and testing of urine by the healthcare professional or user (effectively trained by the healthcare professional) measures urine characteristics (such as pH, dextrose, osmolality) but does not indicate a presence or absence of a urinary tract infection.

While this current practice works, some of the issues posed by this practice have rendered it far less than ideal. More specifically, this practice is recognized by many health care professionals and patients alike as being problematic in that it is inconvenient, since the specimen must be taken to a lab if obtained at home or needs to be obtained in an office/clinic setting, requires a procedure that is subject to error (timing of collecting the specimen, amount of urine collected, possible contamination of collection container and therefore specimen contamination), and it requires significant mobility and dexterity on behalf of the patient. As a result, it is desirable to have a device and collection method which results in obtaining an exact midstream and sterile specimen that could easily be tested.

SUMMARY OF THE DISCLOSURE

Accordingly, the present disclosure is directed to a device for the collection of a urine sample comprising a channel, an opening in the channel, and a collector associated with the opening. The channel is formed so urine can flow through it from a first end to a second end thereof. The opening is provided in the channel at a point between the first and the second ends, and the collector is associated with the opening in the channel for receiving urine therein. Advantageously, a member may cover the opening in the channel to permit urine to pass through it after contact with urine. In particular, the member may be a soluble membrane which dissolves after urine has flowed through the channel for a period of time whereby the collector receives a urine sample not from the initial flow of urine.

As an alternative to a soluble membrane, the member covering the opening in the channel can be a non-soluble membrane which is fixed in place by an adhesive element which reduces in adhesive effectiveness when in contact with liquid (urine), a non-soluble membrane which is fixed in place by an adhesive element which reduces in adhesive effectiveness when its temperature is raised, or a non-soluble membrane which is initially impermeable but increases in permeablity when in contact with liquid (urine).

In one exemplary embodiment, the channel through which urine can flow is defined by a lumen associated with a urinary catheter. The urinary catheter may advantageously include a funnel so that the lumen defining the channel may be located within the funnel. Alternatively, the urinary catheter may have the lumen defining the channel located within the catheter tube.

In another exemplary embodiment, the channel through which urine can flow is the lumen of a test device for connection to a urinary catheter.

As for additional details, the collector associated with the opening in the channel may suitably comprise a urine collection cup surrounding the opening. The collector may alternatively lead to a chamber which is provided for the purpose of testing a urine sample. Still further, the collector may suitably include at least one test means, e.g., a test pad, for receiving and testing urine after the soluble member has dissolved.

The present disclosure is also directed to a method for the collection of a urine sample in a manner avoiding bacteria contamination. The method includes the steps of providing a channel through which urine can flow from a first end to a second end thereof, forming an opening in the channel at a point between the first and the second ends thereof, covering the opening with a soluble member which dissolves after contact with urine, locating a collector externally of the channel in operative association with the opening, and causing urine to flow through the channel for a period of time to causes the soluble member to dissolve. With the method of the disclosure, the collector is capable of receiving a urine sample which is not from the initial flow of urine.

Other objects, advantages, and features of the present disclosure will become apparent from a consideration of the following specification taken in conjunction with the accompanying drawings.

DETAILED DESCRIPTION OF THE PREFERRED DISCLOSURE

Figure 1:
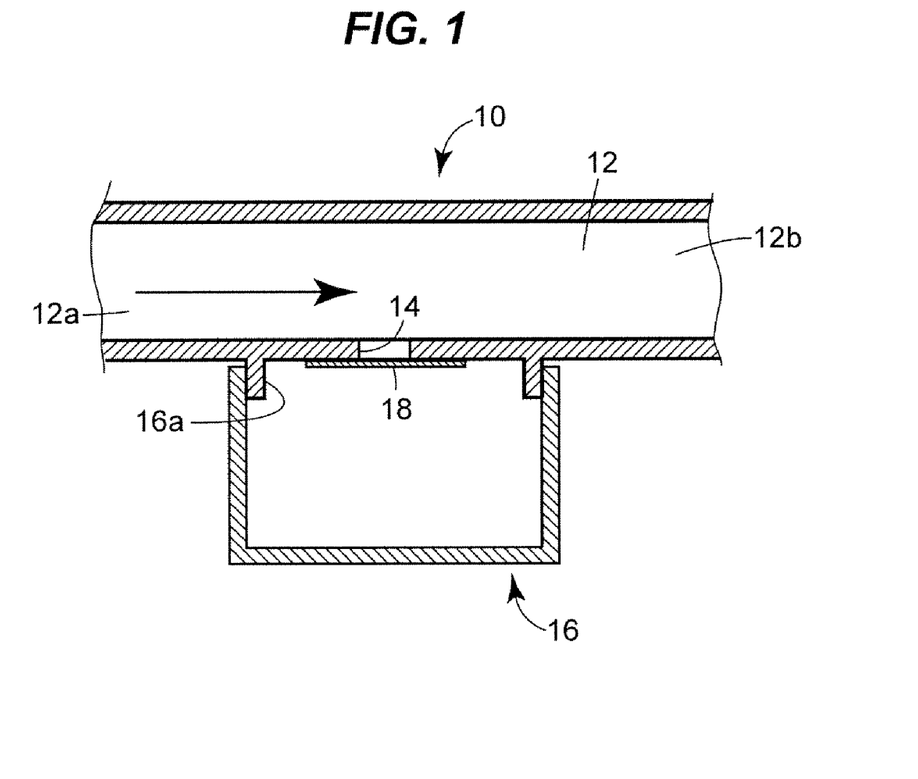
FIG. 1 is a schematic view of a first embodiment of a device for the collection of a urine sample in accordance with the present disclosure.
Figure 2:
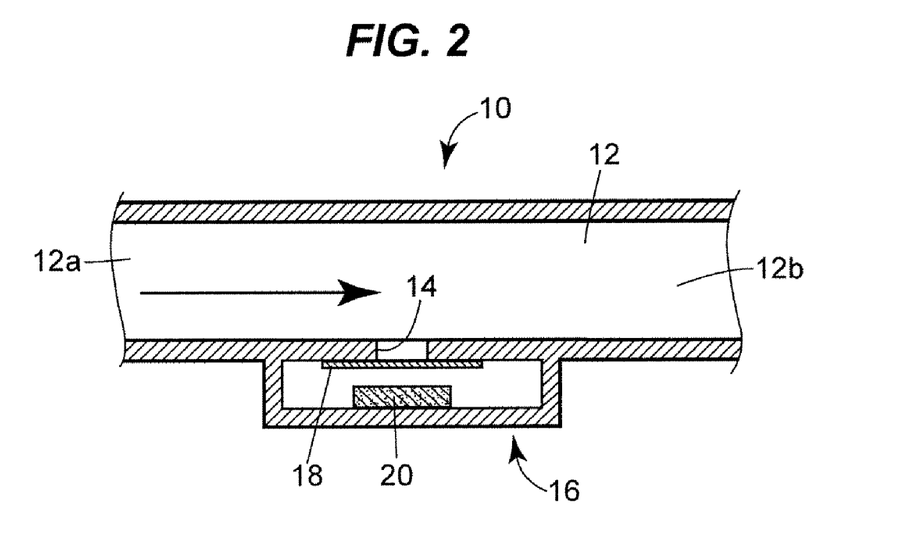
FIG. 2 is a schematic view of a second embodiment of a device for the collection of a urine sample in accordance with the present disclosure.

Referring to the drawings, and first to FIGS. 1 and 2, the reference numeral 10 designates generally a device for the collection of a urine sample. The device 10 includes a channel 12 through which the urine can flow from a first end 12a to a second end 12b. The device 10 also includes an opening 14 in the channel 12 which is located at a point between the first and second ends 12a and 12b. The device 10 further includes a collector 16 associated with the opening 14 in the channel 12 for receiving urine. The device 10 can still further include a member 18 which covers the opening 14 in the channel 12. The member 18 will permit urine to pass through the opening 14 after contact with urine that has flowed through the channel 12 for a period of time. Thus, the collector 16 can receive a urine sample not from the initial flow of urine passing through the channel 12.

Still referring to FIGS. 1 and 2, the collector 16 associated with the opening 14 in the channel 12, as illustrated in FIG. 1, is a urine collection cup surrounding the opening whereas the corresponding collector 16, as illustrated in FIG. 2, is a urine test chamber. In both instances, it is advantageous for the member 18 covering the opening 14 in the channel 12 to comprise a soluble membrane formed of PVOH or any similar type of material that dissolves in urine or otherwise permits urine to pass through the opening after it has been in contact with the member for a period of time. In the test chamber case, the collector 16 has at least one test means 20 such as a test pad or any other similar type of testing device which is capable of receiving and testing urine after the member 18 has permitted urine to pass through the opening 14 (FIG. 2).

As an alternative to the soluble membrane which has been described above, it will be understood that the device can use a non-soluble membrane which is fixed in place by an adhesive element which reduces in adhesive effectiveness when in contact with liquid (urine). For example, the non-soluble membrane may comprise a tape with a water soluble adhesive such as Water-Soluble Wave Solder Tape 5414 sold by 3M Industrial Adhesives and Tape Division. As another alternative, the device can use a non-soluble membrane which is fixed in place by an adhesive element which reduces in adhesive effectiveness when its temperature is raised. For example, any non-soluble membrane can be used which is fixed in place with an adhesive that loses its adhesive effectiveness at or below the typical temperature of urine. As still another example, the device can use a non-soluble membrane which is initially impermeable but increases in permeablity when in contact with liquid (urine). For example, any permeable fabric can be used which is coated with a soluble layer of poly vinyl alcohol or the like.

Figure 3:
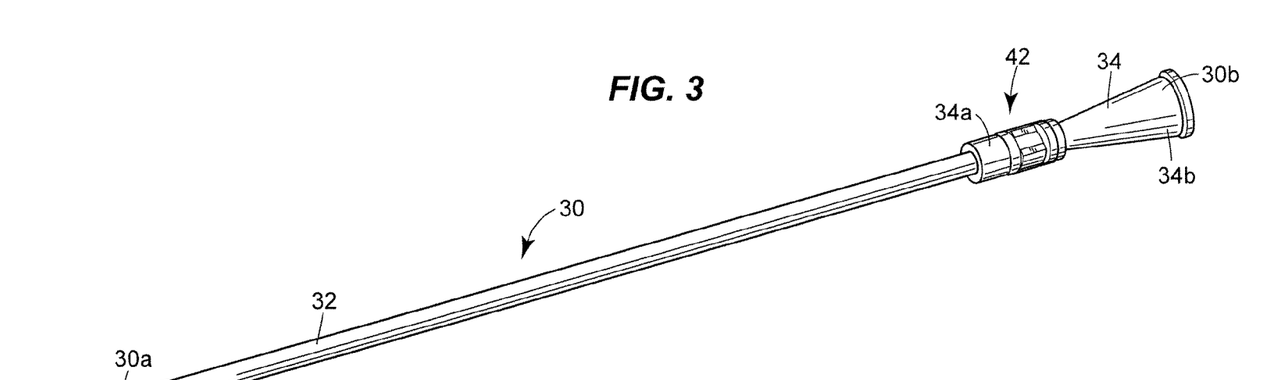
FIG. 3 is an elevational view of a urinary catheter having an integral urine sample collector formed in accordance with the present disclosure.

Referring to FIG. 3, the channel through which urine can flow is advantageously defined by a lumen associated with a urinary catheter generally designated 30. It will be appreciated in connection with the schematic illustrations in FIGS. 1 and 2 that the channel 12 shown therein could be a lumen associated with a urinary catheter or, as will be appreciated from further discussion below, it could be a lumen associated with any related type of device such as a device specifically designed for testing a urine sample. In other words, FIGS. 1 and 2 are merely schematic representations of at least what is shown in the two specific embodiments of the concept set forth in the present disclosure.

Still referring to FIG. 3, the urinary catheter 30 includes a catheter tube 32 and a funnel 34 at one end thereof. The lumen defining the channel 36 is located within the funnel 34, but it also can be located within the catheter tube 32. However, in the illustrated embodiment, the channel 36 is located within the funnel 34 as best shown in FIGS. 5A-5B.

Figure 5A:
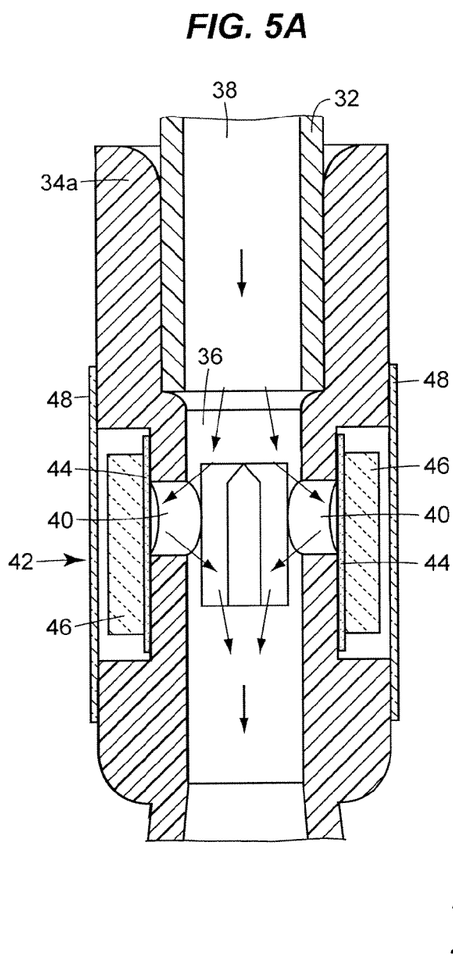
FIG. 5A-5B is a pair of sectional views showing the internal structure of the integral urine sample collector of the urinary catheter of FIG. 3.
Figure 5B:
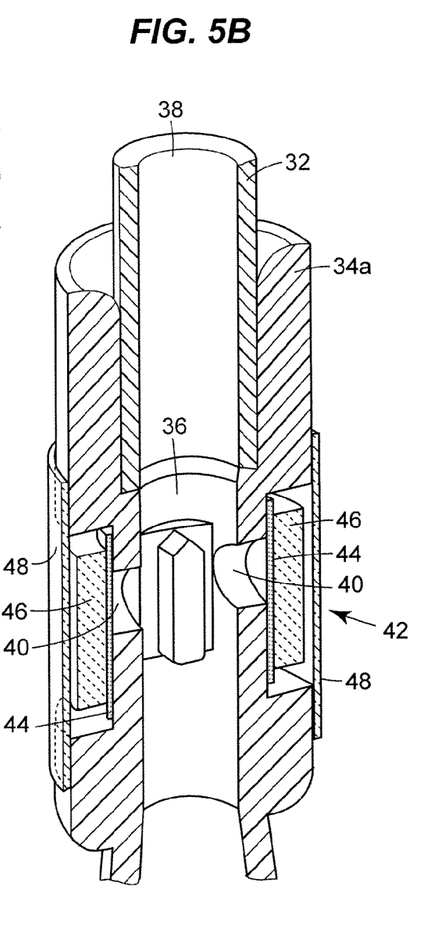

Still referring to FIGS. 5A-5B, the catheter tube 32 will be seen to have its own lumen defining a channel 38 for the flow of urine in direct fluid flow communication with the lumen defining the channel 36. However, it is the channel 36 that has at least one opening 40 which is covered by a soluble member. While not illustrated, the opening 40 could be provided in the catheter tube 32 in which case the opening in the catheter tube would be covered by a soluble member and would have a collector associated therewith.

Figure 7:
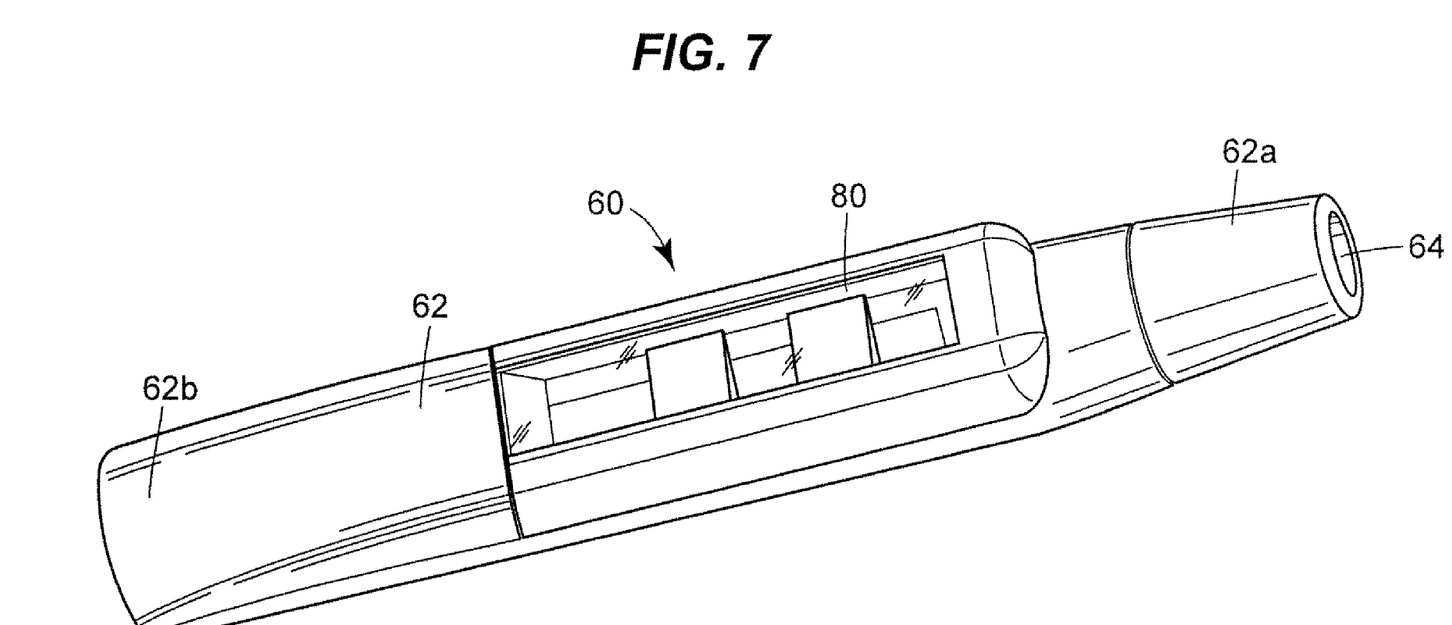
FIG. 7 is an elevational view of a device for testing a urine sample in conjunction with a urinary catheter in accordance with the present disclosure.

Referring to FIG. 7, the channel through which urine can flow is advantageously defined by the lumen of a test device 60 suitable for connection to a urinary catheter to receive a urine sample, and the detailed structure and operation of the test device embodiment as well as the urinary catheter embodiment illustrated in FIG. 3 and preliminarily described above will be set forth in greater detail below.

Referring once again to FIG. 3, and considering it in conjunction with FIGS. 4A-4D, the urinary catheter 30 comprised of the catheter tube 32 and the funnel 34 will be seen to have a urine sample collector 42. It will be appreciated from consideration of FIGS. 3, 5A and 5B, in particular, that the urinary catheter 30 comprises an axially extending body having a lumen defining the respective channels 36 and 38 in the funnel 34 and the catheter tube 32 through which urine can flow from a first end of the catheter 30 as at 30a to a second end thereof as at 30b. As previously described, the channel 36 is in the funnel 34, but it is in axial alignment with the channel 38 in the catheter tube 32 to define a continuous urine flow path from the end 30a to the end 30b of the urinary catheter 30.

Figures 4A, 4B, 4C:
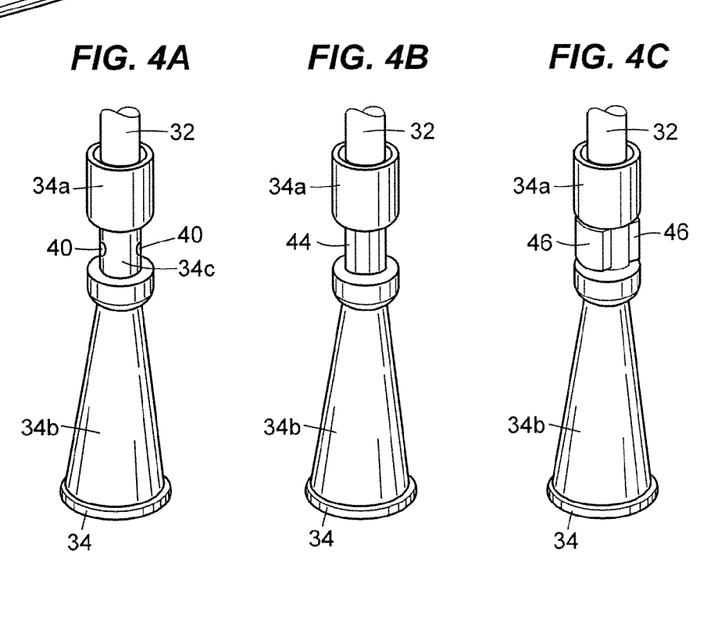
FIGS. 4A-4D is a series of elevational views showing the assembly of the integral urine sample collector of the urinary catheter of FIG. 3.

Referring now to FIGS. 4A, 5A and 5B, the urinary catheter 30 has at least one generally radial opening 40 extending through the axially extending body from the lumen to a point externally of the lumen. In the illustrated embodiment, the urinary catheter 30 has a pair of diametrically opposed radial openings 40 which extend through the lumen defining the channel 36 in the funnel 36. As best shown in FIGS. 5A-5B, the urine collector 42 for receiving a urine sample surrounds the diametrically opposed radial openings 40 externally of the axially extending body (see, also, FIG. 3).

Referring to FIGS. 4B, 5A and 5B, a soluble member 44 covers the generally radial openings 40 and dissolves after being in contact with urine for a period of time. When diametrically opposed radial openings 40 are utilized, they can either be covered by a pair of soluble members 44 or by a single soluble member 44 that can extend circumferentially entirely about the funnel 34 as best shown in FIG. 4B. In either case, the soluble member 44 is such that it will dissolve over a period of time so the urine collector 42 can thereby receive a urine sample which is not from the initial flow of urine.

Figure 4D:
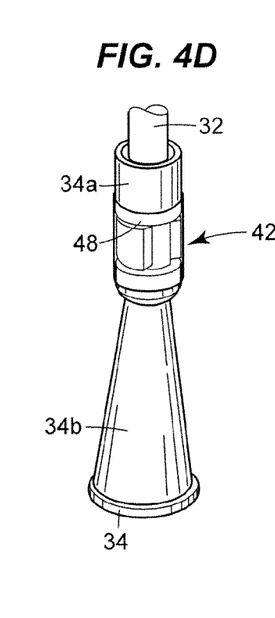

As shown, the funnel 34 includes a first portion 34a of generally uniform diameter secured to the catheter tube 32 and a second portion 34b of outwardly tapering diameter remote from the catheter tube 32. The first portion 34a of generally uniform diameter includes an area of reduced diameter 34c (FIG. 4A) generally intermediate the catheter tube 32 and the second portion 34b of outwardly tapering diameter. The generally radial openings 40 extend into the area of reduced diameter 34c and the soluble member 44 is located within the area of reduced diameter to completely cover the generally radial openings. The urinary catheter 30 also includes one or more test pads 46 located within the area of reduced diameter 34C outwardly of the soluble member 44 for receiving and testing urine (FIGS. 4C, 5A and 5B). Further, the urinary catheter 30 includes a clear waterproof film layer 48 extending about the first portion of generally uniform diameter 34a to cover and seal that area against urine leakage (FIGS. 4D, 5A and 5B).

As previously discussed, the generally radial opening(s) can extend through the catheter tube and the soluble member can be located externally of the catheter tube to cover the generally radial opening(s). In this alternative embodiment, the catheter tube 32 in FIG. 3 would comprise the tube defining the channel 12 in FIGS. 1 and 2, i.e., the tube shown in FIGS. 1 and 2 would comprise a schematic representation of the catheter tube 32 illustrated in FIG. 3. In this regard, the opening 14 in the channel 12 will be located near the end of the catheter opposite the drainage eyes to be outside the urethra when the catheter has been inserted to drain the bladder.

When the tube defining the channel 12 in FIGS. 1 and 2 comprises a catheter tube such as 32 in FIG. 3, the collector 16 can comprise a collection cup removably mounted to a fitting 16a surrounding the opening 14. The collection cup 16 will be removably mounted to the fitting 16a externally of the catheter tube for receiving urine after the soluble member 18 has been dissolved (FIG. 1). Alternatively, the collector 16 can comprise a test chamber externally of the catheter tube which has at least one test pad for receiving and testing urine after the soluble member 18 has been dissolved (FIG. 2).

Figure 8A:
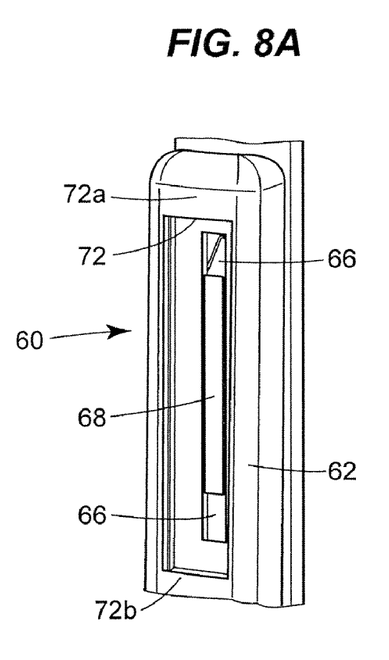
FIG. 8A-8D is a series of elevational views showing the assembly of the device for testing a urine sample with a conventional urinary catheter.
Figure 8B:
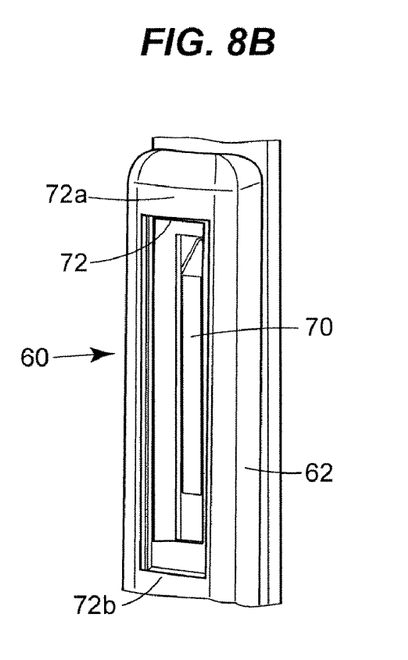
Figure 9A:
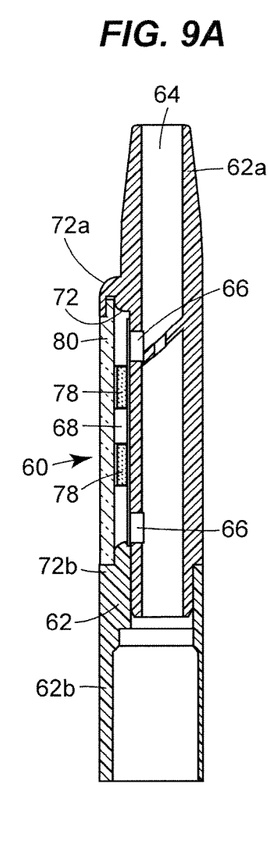
FIG. 9A-9C is a series of sectional views showing the internal structure of the device for testing a urine sample as shown in FIG. 7.
Figure 9B:
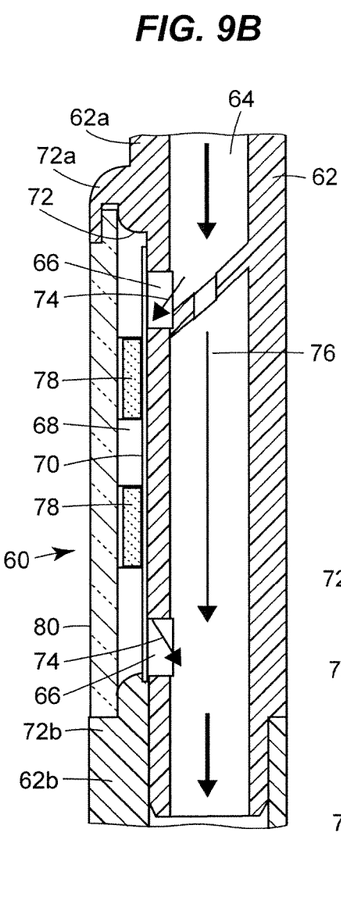

Referring once again to FIG. 7, the test device 60 includes an axially extending body 62 having a lumen defining a main channel 64 through which urine can flow from a first end 62a to a second end 62b. The test device 60 also includes at least one opening 66 extending through the axially extending body 62 from the lumen to a point externally of the lumen as shown in FIGS. 8A and 9A. The test device 60 further includes a collector 68 for receiving urine which communicates with the opening 66 extending through the axially extending body 62 as shown in FIGS. 8A and 9A. The test device 60 still further includes a soluble member 70 covering the opening 66 which dissolves after being in contact with urine for a period of time as shown in FIGS. 8B and 9B. With this arrangement, the test device 60 is well suited for testing a urine sample in view of the fact that the collector 68 is able to receive a urine sample which is not from the initial flow of urine.

In the illustrated embodiment, the axially extending body 62 has a first end 62a which is adapted for connection to a urinary catheter and a second end 62b remote therefrom (FIG. 7). The axially extending body 62 also includes an external recess 72 intermediate the first and second ends 62a and 62b in communication with the opening 66 extending through the axially extending body (FIGS. 8A and 9A). Further, the test device 60 preferably includes a pair of axially spaced openings 66 which extend through the axially extending body 62 so as to be in communication with the external recess 72 which defines the collector 68 generally adjacent opposite ends 72a and 72b (FIGS. 8A and 9B). As will be appreciated from FIGS. 8A and 9B, the external recess 72 defines a channel which extends from one of the axially spaced openings 66 to the other.

In particular, the openings 66 cooperate with the external recess 72 to define a secondary urine flow path or channel that first extends at an angle downwardly and away from a primary urine flow channel, then extends generally parallel to the primary urine flow channel, and then extends at an angle downwardly and toward the primary urine flow channel so that urine flowing along the secondary urine flow path or channel is directed into the collector 68 defined by the external recess 72 (FIGS. 8B and 9B).

Referring specifically to FIG. 9B, the path or channel defined by the external recess 72 will be understood to comprise a major portion of the secondary urine flow path or channel from one of the axially spaced openings 66 to the other of the axially spaced openings 66 as illustrated by the arrows 74 where the arrow 76 illustrates the primary urine flow channel through the test device 60.

Figure 8C:
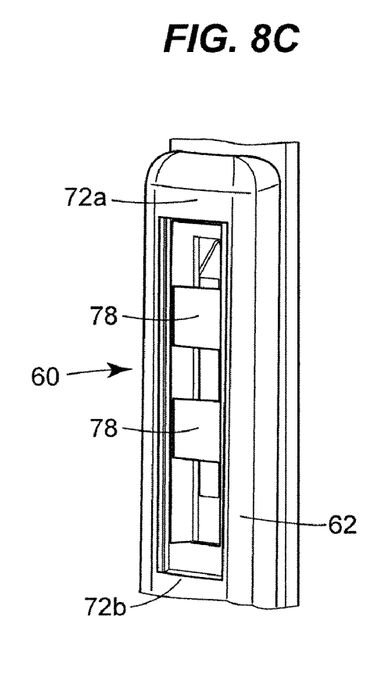

Referring again to FIGS. 8B and 9B, the soluble member 70 will be seen to be disposed within the external recess 72 of the axially extending body 62 to cover both of the axially spaced openings 66. It will also be seen from FIGS. 8C and 9B that the test device 60 preferably includes one or more test means such as the pads 78 located within the external recess 72 outwardly of the soluble member 70 for receiving and testing urine after the soluble member has been dissolved by urine flow. As illustrated, the test means or pads 78 are disposed within the external recess 72 within the secondary urine flow path or channel for receiving and testing urine after the soluble member 70 has been dissolved by urine.

Figure 8D:
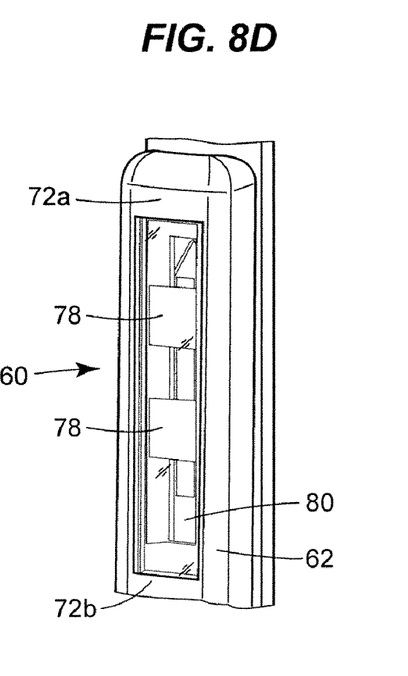
Figure 9C:
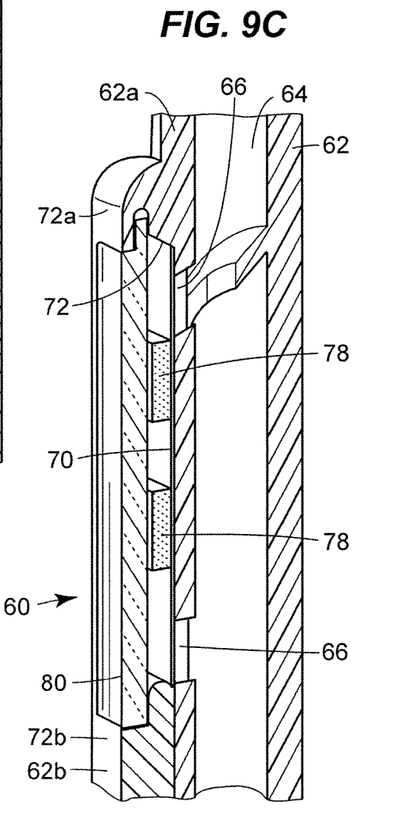

Referring now to FIGS. 8D and 9C, the test device 60 further includes a waterproof transparent body 80 extending over the external recess 72 of the axially extending body 62 in a manner covering and sealing the external recess 72 against leakage of urine from the device. In other words, the waterproof transparent body 80 restricts the flow of urine to the secondary urine flow path or channel so urine must flow in one of the axially spaced openings 66, through the external recess 72, and then out the other of the axially spaced openings 66. In addition, the test device 60 is preferably formed such that the first end 62a of the axially extending body 62 can be connected to the funnel end of a urinary catheter and the second end 62b of the axially extending body can be connected directly to a urine collection bag.

Figure 6:
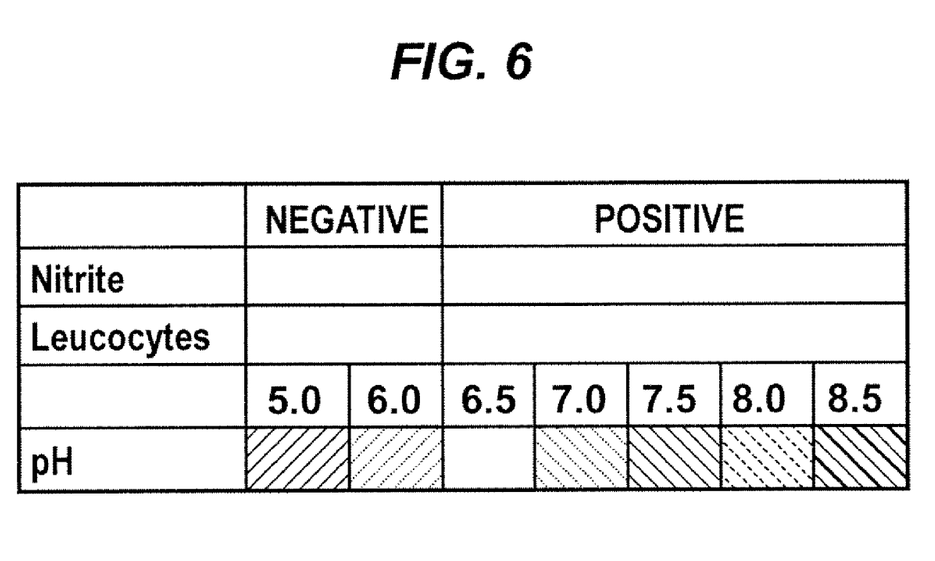
FIG. 6 is a representative chart for reading the results from a pair of test pads incorporated into the integral urine sample collector shown in FIG. 3.

From the foregoing, it will be appreciated that initial urine flow does not access the test means or pads in any of the embodiments but, rather, serves to dissolve the soluble member whereby only subsequent urine flow is absorbed into the test pads. The test means when in the form of pads will change color depending on the result of the urine test, and the color change can be observed through the clear waterproof film layer or transparent body 80. After observing the color change in the test pad(s), the resulting color of the test pad(s) is then compared to a color card which may, by away of example only, be a color card for nitrite, leucocytes and pH such as the type which is shown in black and white in FIG. 6.

In accordance with the present disclosure, a method for the collection of a urine sample is provided which includes the steps of providing a channel through which urine can flow from a first end to a second end and forming an opening in the channel at a point between the first and second ends. The method also includes the steps of covering the opening with a member which permits urine to pass through the opening after it has been in contact with urine for a period of time and locating a collector externally of the channel so as to be in operative association with the opening. Further, the method includes the step of causing urine to flow through the channel for a period of time to permit urine to pass through the opening so the collector can receive a urine sample not from the initial flow of urine.

In other respects concerning the method, the channel through which urine can flow is suitably defined by a lumen associated with a urinary catheter. The urinary catheter may include a funnel in which case the lumen defining the channel may be located within the funnel or, alternatively, the lumen defining the channel may be located within the catheter tube. As a further alternative, the channel through which urine can flow may be the lumen of a test device for connection to a urinary catheter.

In still other respects concerning the method, the collector associated with the opening in the channel may be a urine collection cup surrounding the opening, or it may lead to a urine test chamber. Still additionally, the member covering the opening in the channel may comprise a soluble membrane formed of PVOH or another material having the requisite characteristic of being dissolvable or otherwise permitting urine to pass through the opening after being in contact with urine for a period of time. Moreover, the method contemplates the collector including one or more test pads for receiving and testing urine after the member permits urine to pass through the opening from being in contact with urine.

While the foregoing sets forth a detailed description of the preferred disclosure, it will be appreciated by those skilled in the art that the details herein given may be varied without departing from the true spirit and scope of the disclosure as set forth in the appended claims.

What is claimed is:

1. A device for collecting a urine sample, comprising:
   an axially extending body having a channel defining a continuous flow path extending from a first end to a second end thereof and through which urine can flow;
   a generally radial opening in the axially extending body extending from a point in communication with the continuous flow path to a point externally of the axially extending body at a location intermediate the first and the second ends thereof;
   a collector associated with the generally radial opening externally of the axially extending body for receiving urine; and
   a member covering the generally radial opening in the axially extending body which permits urine to pass from the continuous flow path defined by the channel, through the generally radial opening in the axially extending body, and into the collector only after the member has been in contact with urine that has passed through the continuous flow path defined by the channel for a period of time;
   whereby, the collector is only able to receive a urine sample which is not from an initial flow of urine at a location externally of the axially extending body.

2. The device of claim 1 wherein the channel defining the continuous flow path through which urine can flow comprises a lumen associated with a urinary catheter.

3. The device of claim 2 wherein the urinary catheter includes a funnel and the lumen is located within the funnel.

4. The device of claim 2 wherein the urinary catheter includes a catheter tube and the lumen is located within the catheter tube.

5. The device of claim 1 wherein the channel defining the continuous flow path through which urine can flow comprises a lumen of a test device for connection to a urinary catheter.

6. The device of claim 1 including a urine collection bag associated with the second end of the continuous flow path through which urine can flow.

7. The device of claim 1 wherein the collector associated with the generally radial opening externally of the axially extending body is a urine collection cup surrounding the opening.

8. The device of claim 1 wherein the collector associated with the generally radial opening externally of the axially extending body comprises a urine test chamber.

9. The device of claim 1 wherein the member covering the generally radial opening in the axially extending body is a soluble membrane formed of PVOH.

10. The device of claim 1 wherein the member covering the generally radial opening in the axially extending body is a non-soluble membrane fixed in place by an adhesive element which reduces in adhesive effectiveness when in contact with liquid.

11. The device of claim 1 wherein the member covering the generally radial opening in the axially extending body is a non-soluble membrane fixed in place by an adhesive element which reduces in adhesive effectiveness when the adhesive element temperature is raised.

12. The device of claim 1 wherein the member covering the generally radial opening in the axially extending body is a non-soluble membrane which is initially impermeable but increases in permeability when in contact with liquid.

13. The device of claim 9 wherein the collector externally of the axially extending body includes at least one test means for receiving and testing urine after the soluble membrane has dissolved.

14. A urinary catheter having a urine sample collector, comprising:
   a catheter tube having a funnel at one end thereof;
   an axially extending body comprising a portion of one of the catheter tube and the funnel and having a lumen defining a channel comprising a continuous flow path through which urine can flow;
   a generally radial opening in the axially extending body extending from a point in communication with the continuous flow path to a point externally of the axially extending body;
   a urine collector for receiving urine surrounding the generally radial opening externally of the axially extending body; and
   a member covering the generally radial opening in the axially extending body which permits urine to pass from the continuous flow path, through the generally radial opening, and into the urine collector only after the member has been in contact with urine that has passed through the continuous flow path for a period of time;
   whereby, the urine collector is only able to receive a urine sample which is not from an initial flow of urine at a location externally of the axially extending body.

15. The urinary catheter of claim 14 wherein the axially extending body comprises a portion of the funnel and the lumen is located within the funnel.

16. The urinary catheter of claim 15 wherein the funnel includes a first portion of generally uniform diameter secured to a catheter tube and a second portion of outwardly tapering diameter remote from the catheter tube.

17. The urinary catheter of claim 16 wherein the first portion of generally uniform diameter includes an area of reduced diameter generally intermediate the catheter tube and the second portion of outwardly tapering diameter.

18. The urinary catheter of claim 17 wherein the generally radial opening extends into the area of reduced diameter, and the member covering the generally radial opening is located within the area of reduced diameter.

19. The urinary catheter of claim 18 wherein the member is selected from one of a soluble membrane which dissolves after being in contact with urine for a period of time, a non-soluble membrane fixed in place by an adhesive element which reduces in adhesive effectiveness when in contact with liquid, a non-soluble membrane fixed in place by an adhesive element which reduces in adhesive effectiveness when the adhesive element temperature is raised, and a non-soluble membrane which is initially impermeable but increases in permeability when in contact with liquid.

20. The urinary catheter of claim 18 including a test chamber surrounding the generally radial opening externally of the funnel and containing at least one test means for receiving and testing urine after the member permits urine to pass through the generally radial opening.

21. The urinary catheter of claim 19 wherein the urine collector comprises a collection cup removably mounted to a fitting surrounding the generally radial opening externally of the funnel for receiving urine after the member permits urine to pass through the generally radial opening.

22. The urinary catheter of claim 19 including a test means located within the area of reduced diameter outwardly of the member wherein the test means is adapted to receive and test urine after the member permits urine to pass through the generally radial opening.

23. The urinary catheter of claim 22 including a clear waterproof film layer extending about the first portion of generally uniform diameter outwardly of the test means so as to cover and seal the area of reduced diameter against urine leakage.

24. The urinary catheter of claim 14 wherein the axially extending body comprises a portion of the catheter tube and the lumen is located within the catheter tube.

25. The urinary catheter of claim 24 wherein the generally radial opening extends through the catheter tube and the member is located externally of the catheter tube to initially cover the generally radial opening.

26. The urinary catheter of claim 25 wherein the member is selected from one of a soluble membrane which dissolves after being in contact with urine for a period of time, a non-soluble membrane fixed in place by an adhesive element which reduces in adhesive effectiveness when in contact with liquid, a non-soluble membrane fixed in place by an adhesive element which reduces in adhesive effectiveness when the adhesive element temperature is raised, and a non-soluble membrane which is initially impermeable but increases in permeability when in contact with liquid.

27. The urinary catheter of claim 25 wherein the urine collector comprises a test chamber surrounding the generally radial opening externally of the catheter tube and containing at least one test means for receiving and testing urine after the member permits urine to pass through the generally radial opening.

28. The urinary catheter of claim 26 wherein the urine collector comprises a collection cup removably mounted to a fitting surrounding the generally radial opening externally of the catheter tube for receiving urine after the member permits urine to pass through the generally radial opening.

29. A device for testing a urine sample, comprising:

an axially extending body having a lumen defining a main channel comprising a continuous flow path through which urine can flow;

at least one generally radial opening in the axially extending body extending from a point in communication with the continuous flow path to a point externally of the axially extending body;

a urine collector for receiving urine surrounding the at least one generally radial opening externally of the axially extending body; and a member covering the at least one generally radial opening in the axially extending body which permits urine to pass from the continuous flow path comprising the main channel, through the at least one generally radial opening, and into the urine collector only after the member has been in contact with urine that has passed through the continuous flow path comprising the main channel for a period of time;

whereby, the urine collector is only able to receive a urine sample which is not from an initial flow of urine at a location externally of the axially extending body.

30. The testing device of claim 29 wherein the axially extending body has a first end for connection to a urinary catheter and a second end remote therefrom.

31. The testing device of claim 30 wherein the urine collector comprises an external recess in the axially extending body intermediate the first and second ends in communication with the continuous flow path through the at least one generally radial opening.

32. The testing device of claim 31 including a pair of axially spaced generally radial openings extending through the axially extending body through which the continuous flow path is in communication with the external recess generally adjacent opposite ends of the external recess.

33. The testing device of claim 32 wherein the external recess defines a secondary urine flow channel extending from one of the axially spaced generally radial openings to the other of the axially spaced generally radial openings.

34. The testing device of claim 33 wherein the member which permits urine to pass through the at least one generally radial opening after the member is in contact with urine for a period of time is disposed within the external recess of the axially extending body to cover both of the axially spaced generally radial openings.

35. The testing device of claim 34 including at least one test means located within the external recess outwardly of the member which permits urine to pass through the at least one generally radial opening for receiving and testing urine.

36. The testing device of claim 35 including a waterproof transparent body extending over the external recess of the axially extending body in a manner covering the at least one test means and sealing the external recess against urine leakage.

37. The urinary catheter of claim 29 wherein the member is selected from one of a soluble membrane which dissolves after being in contact with urine for a period of time, a non-soluble membrane fixed in place by an adhesive element which reduces in adhesive effectiveness when in contact with liquid, a non-soluble membrane fixed in place by an adhesive element which reduces in adhesive effectiveness when the adhesive element temperature is raised, and a non-soluble membrane which is initially impermeable but increases in permeability when in contact with liquid.

38. The testing device of claim 29 wherein the axially extending body has a first end for connection to a urinary catheter and a second end for connection to a urine collection bag.

39. A method for collecting a urine sample, comprising a plurality of steps including the steps of:
- providing an axially extending body having a channel defining a continuous flow path extending from a first end to a second end thereof and through which urine can flow;
- forming a generally radial opening in the axially extending body extending from a point in communication with the continuous flow path to a point externally of the axially extending body at a location intermediate the first and second ends thereof;
- locating a collector externally of the axially extending body so as to be associated with the generally radial opening for receiving urine;
- covering the generally radial opening in the axially extending body with a member which permits urine to pass from the continuous flow path defined by the channel, through the generally radial opening in the axially extending body, and into the collector only after the member has been in contact with urine that has passed through the continuous flow path defined by the channel for a period of time; and
- causing urine to flow through the continuous flow path defined by the channel for the period of time until the member permits urine to pass from the continuous flow path through the generally radial opening in the axially extending body into the collector;
- whereby, the collector is only capable of receiving a urine sample which is not from an initial flow of urine at a location externally of the axially extending body.

40. The method of claim 39 wherein the axially extending body having the channel defining the continuous flow path through which urine can flow comprises a lumen associated with a urinary catheter.

41. The method of claim 40 wherein the urinary catheter includes a funnel and the lumen is located within the funnel.

42. The method of claim 40 wherein the urinary catheter includes a catheter tube and the lumen is located within the catheter tube.

43. The method of claim 39 wherein the axially extending body having the channel defining the continuous flow path through which urine can flow comprises a lumen of a test device for connection to a urinary catheter.

44. The method of claim 39 wherein the collector associated with the generally radial opening externally of the axially extending body is a urine collection cup surrounding the generally radial opening.

45. The method of claim 39 wherein the collector associated with the generally radial opening externally of the axially extending body comprises a urine test chamber.

46. The method of claim 39 wherein the member is selected from one of a soluble membrane which dissolves after being in contact with urine for a period of time, a non-soluble membrane fixed in place by an adhesive element which reduces in adhesive effectiveness when in contact with liquid, a non-soluble membrane fixed in place by an adhesive element which reduces in adhesive effectiveness when the adhesive element temperature is raised, and a non-soluble membrane which is initially impermeable but increases in permeability when in contact with liquid.

47. The method of claim 46 wherein the member is a soluble membrane and the collector includes at least one test means for receiving and testing urine after the soluble membrane has dissolved.

* * * * *